United States Patent [19]

Clarkson, Jr. et al.

[11] Patent Number: 5,462,969

[45] Date of Patent: Oct. 31, 1995

[54] METHOD AND COMPOSITIONS FOR TREATMENT OR PREVENTION OF PNEUMOCYSTIC CARINII INFECTIONS

[75] Inventors: Allen B. Clarkson, Jr., New York, N.Y.; Robert W. Grady, Kinnelon, N.J.

[73] Assignee: New York University, New York, N.Y.

[21] Appl. No.: 192,404

[22] Filed: Feb. 4, 1994

Related U.S. Application Data

[62] Division of Ser. No. 910,714, Jul. 7, 1992, Pat. No. 5,302,598, which is a division of Ser. No. 340,344, Apr. 19, 1989, Pat. No. 5,158,979.

[51] Int. Cl.$^6$ .................. A61K 31/19; A61K 31/155
[52] U.S. Cl. .............................. 514/575; 514/637
[58] Field of Search ........................ 514/575, 637

[56] References Cited

U.S. PATENT DOCUMENTS

| | | | |
|---|---|---|---|
| 2,410,796 | 11/1986 | Newberry et al. | 260/501 |
| 3,049,544 | 8/1962 | Stenbuck et al. | 260/256.4 |
| 3,341,541 | 9/1967 | Hoffer | 260/256.4 |
| 4,419,365 | 12/1983 | McLachlan | 424/320 |
| 4,614,797 | 11/1986 | Nagata et al. | 540/226 |

OTHER PUBLICATIONS

Allegra et al., (1987), *New England Journal of Medicine*, 317:978–985.
Boelaert et al., (1991), *Am. J. Kidney Dis.*, 18:660–667.
Carotenuto et al., (1986), *J. of Immunol.*, 136:2342–2347.
Chiu et al., (1986), *Brit. Med. J.*, 292:97.
Clarkson et al., (1988), *Antimicrobial Agents and Chemotherapy*, 32:1158–1163.
Daly et al., (1989), *Am. J. Med.*, 87:468–471.
Edman et al., (1988), *Nature*, 334:519–522.
Fritsch et al., (1985), *Exp. Parisitol*, 60:171–174.
Gallacher et al., (1989), *Critical Care Medicine*, 17:104–105.
Gallant et al., (1986), *New Eng. J. Med.*, 341 [25]:1653.
Graziano et al., (1978), *J. Ped.*, 92(4):648–652.
Green et al., (1988), *British Journal of Clinical Pharmacology*, 487–491.
Haverkos, (1984), *Am. J. Med.*, 76:501–508.
Hughes, (1987), *N. Eng. J. Med.*, 317:1021–1023.
Hynes, (1970), *J. Med. Chem.*, 13:1235–1237.
Jones et al., (1983), *Eur. J. Clin. Microbiol.*, 2:411–413.
Jones et al., (1987), *Nature*, 267:63–64.
Kouides et al., (1988), *Brit. J. Haematol.*, 70:382–383.
Kovacs et al., (1988), *Journal of Infectious Diseases*, 158:254–259.
Lederman et al., (1984), *Blood*, 64:748–753.
Lowy et al., (1984), *Animicrob. Agents Chemotherap.* 25 [3.
Masawe et al., (1974), *Lancet*, 2:314–317.
Mazzoleni et al., (1991), *Diges. Dis. and Sci.*, 36:1155–1160.
Peto et al., (1986), *Br. J. Haematol.*, 63:273–280.
Pollack et al., (1987), *Proc. Soc. Exp. Biol. Med.*, 184:162–164.
Queener et al., (1987), *Antimicrobial Agents and Chemotherapy*, 31:1323–1327.
Queener et al., (1988), *Antimicrobial Agents and Chemotherapy*, 32:807–813.
Raventos–Suraez et al., (1982), *Am. J. Trop. Med. Hyg.*, 3(5):919–922.
Schafer et al., (1985), *Arch. Intern. Med.*, 145:1217–1221.
Sattler et al., (1988), *Annals of Internal Medicine*, 109:208–287.
Vandenbergh et al., (1983), *App. and Environ. Micro.*, 46 [.
Weinberg et al., (1986), *Blood*, 68:286A.
Youdim, *Am. Rev. Resp. Dis.*, 99:925–931 (Abstract only) (1969).

*Primary Examiner*—Zohreh Fay
*Attorney, Agent, or Firm*—Darby & Darby

[57] ABSTRACT

The present invention provides methods for treating and preventing the onset of *Pneumocytis carinii* pneumonia (PCP) comprising administering to a mammal in need of such treatment or prevention an effective amount of a pharmaceutically acceptable iron chelator. This invention also provides a method for treating or preventing the onset of PCP comprising administering to a mammal in need of such treatment or prevention a composition comprising the following components: (a) a pharmaceutically acceptable iron chelator; (b) a compound selected from trimethoprim/sulfamethoxazole and pentamidine; and (c) a pharmaceutically compatible carrier or diluent, wherein the amounts of said component (a) and said component (b) in combination are effective in treating said pneumonia. Also provided is a composition for the treatment or prevention of PCP.

5 Claims, No Drawings

METHOD AND COMPOSITIONS FOR TREATMENT OR PREVENTION OF PNEUMOCYSTIC CARINII INFECTIONS

This is a division of application Ser. No. 07/910,714, filed Jul. 7, 1992, now U.S. Pat. No. 5,302,598, which is a division of application Ser. No. 340,344, filed Apr. 19, 1989 (now U.S. Pat. No. 5,158,979 issued Oct. 27, 1992).

BACKGROUND OF THE INVENTION

This invention relates to methods and compositions for treating and/or preventing *Pneumocystis carinii* infections in mammals.

*P. carinii* pneumonitis (PCP) is one of the leading causes of death of victims of acquired immunodeficiency syndrome (AIDS). Untreated, the mortality rate of PCP in AIDS patients approaches 100%. During 1986, the number of deaths from PCP in the United States exceeded the combined number of deaths from all types of meningococcal infections, viral hepatitis and encephalitis, gonorrhea, syphilis, varicella, measles, mumps, rubella, diphtheria, tetanus, pertussis, polio, amebiasis, shigellosis, salmonellosis, typhoid fever, typhus fever, cholera, rabies, brucellosis, anthrax, tularemia, botulism, and malaria. The clinical course of PCP infection in immunosuppressed patients presents a number of symptoms including tachypnea, cough, fever, hypoxemia (blood oxygen deficiency), an increased alveolar-capillary oxygen gradient, respiratory acidosis and bilateral diffuse alveolar disease (Hughes, W. T., *N. Eng. J. Med.*, 317: 1021–1023, 1987).

PCP is caused by a ubiquitous lung dwelling organism. Recent evidence indicates that this pathogen may be a fungus rather than a protozoan as previously thought (Meshnick, S. et al., "Antioxidant Enzymes of *Pneumocystis carinii*", Abstracts from the 36th Annual Meeting of the American Society of Tropical Medicine and Hygiene, p. 235, 1987; Edman, J. C. et al., *Nature* 334: 519–522, 1988; Stringer et al., "Sequence from Ribosomal RNA from *Pneumocystis carinii* compared to those of Four Fungi Suggests an Ascomycetous Affinity", *Journal of Protozoology* 36: 14S-16S, 1989; Watanabe et al., "5S Ribosomal RNA Sequence of *Pneumocystis carinii* and its Phylogenetic Association with )Rhizopoda/Myxomycota/Zygomycota Group", *Journal of Protozoology* 36: 16S-18S, 1989; Edman et al., "Ribosomal RNA Genes of *Pneumocystis carinii*", *Journal of Protozoology* 36: 18S-20S, 1989).

Early potential treatments for the disease were tested on the infantile *P. carinii* interstitial plasma-cell pneumonitis that occurred in epidemic form in Europe. The mortality rate for the untreated form of the affliction was about 50%. At that time, it was determined that various antibiotics and/or anti-microbial agents, such as penicillin, tetracycline, chloramphenicol, streptomycin, quinacrine, chloroquine, neoarsphenamine, stibophen, pamaquine, mulsin, neospiran, arsaphen, arsphenamine, quinine, chloroguanide and emetine hydrochloride were ineffective in treating the disease (Hughes, W., *Pneumocystis carinii* Pneumonitis, CRC Press Incorporated, 1987).

Defined high risk groups exist for PCP. While the ubiquitous *P. carinii* acts as a commensal organism and does not cause disease in a healthy individual, it may nevertheless produce PCP in, for example, patients immunosuppressed due to AIDS, to drugs given for cancer treatment, to drugs given to prevent rejection of organ or tissue transplant, to drugs given for treatment of autoimmune disease and other immunocompromised, i.e., partially or totally immunosuppressed or immunodeficient, patients or hosts. Because PCP poses such a threat to these identifiable high risk groups, there exists a need for a prophylactic routine as well as a therapeutic treatment.

The development of treatments for PCP has been hindered by the lack of knowledge about the biology and properties of the *P. carinii* organism. The nutritional requirements, metabolic pathways, mode of replication, enzyme systems and taxonomy of *P. carinii* are not well understood. Although there are some newly identified agents active against PCP, only two recognized treatments currently exist for the control of PCP.

The first recognized mode of treatment involves the use of pentamidine, p,p'-(pentamethylenedioxy)dibenzamidine bis(beta-hydroxy-ethanesulfonate) which is an aromatic diamidino compound. Pentamidine may be prepared according to the disclosure in Newberry Easson, U.S. Pat. No. 2,410,796 and is available commercially, e.g., from LyphoMed, Inc., Rosemont, Ill. 60018).

The second treatment involves the use of a combination of trimethoprim with sulfamethoxazole (TMP/SMZ), i.e., 5-[(3,4,5-trimethoxyphenyl)methyl] -2,4-pyrimidinediamine/4-amino-N-(5-methyl-3-isoxazolyl)benzenesulfonamide). TMP may be prepared from guanidine and beta-ethoxy-3,4,5-trimethoxybenzylbenzalnitrile (see, e.g., Stenbuck, Hood, U.S. Pat. No. 3,049,544 and Hoffer, U.S. Pat. No. 3,341,541). SMZ may be prepared starting with ethyl 5-methylisoxazole-3-carbamate (see Kano et al., U.S. Pat. No. 2,888,455). TMP and SMZ, including the combination of TMP/SMZ, are available commercially from a number of sources. For example, a suspension of TMP/SMZ (400 mg/200 mg) is available from Geneva Generics, Inc., Broomfield, Colo. 80020; in tablet form, TMP/SMZ may be obtained from Par Pharmaceutical, Inc., Spring Valley, N.Y. 10977. Other forms of TMP/SMZ-including commercial sources may be found by referring to *Physician's Desk Reference*, 1988 Edition, Med. Econ. Co., Inc., Oradell, N.J., p.325, col. 2.

The efficacy of the combination of TMP/SMZ derives from the ability of TMP to inhibit microbial dihydrofolate reductase activity and from the competitive interference of SMZ with the incorporation of para-aminobenzoic acid into dihydrofolate, which serves to limit the formation of substrate for the enzyme. Known disadvantages of these treatments include lack of clinical responsiveness, high rates of toxicity and numerous other adverse side-effects. In AIDS patients, in particular, the severe adverse reactions caused by pentamidine therapy include neutropenia, thrombocytopenia, rash and alterations in mental state, e.g., depression. Symptoms resulting from pentamidine therapy include hypoglycemia, hypotension and nephrotoxicity. In addition, it has been determined that AIDS patients suffering from PCP require therapy far longer periods of time and have higher relapse rates (Havertos, H. W., *Am. J. Med.* 76: 501–508, 1984).

New treatments undergoing clinical trials include various agents with modes of action similar to that of TMP/SMZ; i.e., interference with folate metabolism. These include: TMP in combination with dapsone, diaminodiphenylsulfone, a drug used to treat leprosy (Green et al., "AIDS-Related *Pneumocystis carinii* Pneumonia Successfully Treated with Dapsone-Trimethoprim", *British Journal of Clinical Pharmacology* 26: 487–491, 1988); trimetrexate (a new anti-cancer drug) in combination with leucovorin as a rescue agent for host metabolism (Allegra et al., "Trimetrexate for the Treatment of *Pneumocystis carinii* Pneumonia in Patients with Acquired Immunodeficiency Syndrome", *New England Journal of Medicine* 317: 978–985, 1987); high doses of steroids combined with specific anti-PCP therapy (Gallacher et al., "Treatment of Acute *Pneumocystis carinii* Pneumonia with Corticosteroids in a Patient with Acquired Immunodeficiency Syndrome", *CritiCal Care Medicine* 17: 104–105, 1989); administration of TMP/SMZ with careful monitoring of the serum concentration in individual patients during treatment so as to minimize adverse side effects (Sattler et al., "Trimethoprim-Sulfamethoxazole Compared with Pentamidine for Treatment of *Pneumocystis carinii* Pneumonia in the Acquired Immunodeficiency Syndrome", *Annals of Internal Medicine* 109: 280–287, 1988). TMP/SMZ has been administered prophylactically to AIDS patients to prevent PCP similar to the protocol found to be successful for children undergoing treatment for leukemia. Pentamidine has been formulated as an aerosol for delivery directly to the lungs primarily as a prophylactic protocol (Kovacs and Masur, "*Pneumocystis carinii* Pneumonia: Therapy and Prophylaxis", *Journal of Infectious Diseases* 158: 254–259, 1988). DL-alphadifluoromethylornithine (DFMO, eflornithine) is based on an entirely new mode of action and is under clinical evaluation for treatment of PCP (Schechter et al., "Clinical Aspects of Inhibition of Ornithine Decarboxylase with Emphasis on Therapeutic Trials of Eflornithine (DFMO) in Cancer and Protozoan diseases", in *Inhibition of Polyamine Metabolism* eds: McCann, Pegg and Sjoerdsma, Academic Press, pages 345–364, 1987). In addition to the new treatments described above, several others have been found to be active in animal models of PCP. These include: compounds related to pentamidine such as berenil (Clarkson et al., "Efficacy of DL-alphadifluoromethylornithine in a Rat Model of *Pneumocystis carinii* Pneumonia", *Antimicrobial Agents and Chemotherapy* 32: 1158–1163, 1988) and 1,4-di(4'-amidinophenoxy)butane (Tidwell et al., "Treatment of Experimental *Pneumocystis carinii* Pneumonia with Analogues of Pentamidine", *Journal of Protozoology* 36: 74s–77s, 1989); piritrexim, another anti-cancer drug which interferes with folate metabolism and is closely related to trimetrexate (Queener et al., "Activity of Lipid-Soluble Inhibitors of Dihydrofolate. Reductase against *Pneumocystis carinii* in Culture and in a Rat Model of Infection", *Antimicrobial Agents and Chemotherapy* 31: 1323–1327, 1987); and a combination of clindamycin and primaquine (Queener et al., "Activity of Clindamycin and Primaquine against *Pneumocystis carinii* in vitro and in vivo", *Antimicrobial Agents and Chemotherapy* 32: 807–813, 1988.

It has long been known that in many instances hosts and pathogens compete for trace nutrients such as iron, and that the ability of a pathogen to establish infection is often dependent on the ability of the pathogen to compete successfully against the host for trace nutrients (Jones, R. and Grady, R. W., *Eur. J. Clin. Microbiol.* 2:411–413, 1983). In order to secure needed iron, many microorganisms produce and release extremely effective, low molecular weight iron chelators known as siderophores, which compete with host iron-binding proteins. The microbe-produced siderophores allow the pathogens to survive the hypoferemia the host produces in response to infection. The host increases the amount of iron-binding proteins such as lactoferrin and transferrin which sequester iron making it unavailable to the microbe. When the microbe-produced siderophores complex with iron, the complex can be taken up by the microbe thus satisfying its nutritional requirement for iron.

Accordingly, it is known that a low bioavailable iron level may contribute to reducing susceptibility to certain microorganisms. It has also been reported that administration of iron compounds to patients suffering from certain diseases aggravates the condition (Masawe, A. E. J., et al., *Lancet*, 2: 314–317, 1974). Therefore, iron chelators, which act to complex iron, have long been known to have therapeutic potential. One use of iron chelators has been to treat iron overload in patients receiving multiple blood transfusions (such as those suffering from beta-thalassemia). Iron chelators have also been used as antibacterial and antimicrobial agents. For example, hydroxamic acids, a specific class of iron chelator, have been found to inhibit malaria sporozoites (Hynes, J. B., *J. Med. Chem.* 13: 1235–1237, 1970). Iron chelators have also been used in conjunction with antimicrobial agents in the control of *Stapbylococcus epidermidis, Escherichia coli, Klebsiella pneumoniae, Proteus mirabilis*, and species of Salmonella, Enterobacter, Pseudomonas and Providencia (van Asbeck, B. et al., *Eur. J. Clin. Microbiol.* 2: 432–438, 1983). Although iron chelators have been employed to treat various microbial infections, their use is by no means predictable or uniformly effective. As an example, desferrioxamine, a hydroxamic acid iron chelator, has been shown to increase the virulence of *S. typhimurium* in mice (Jones, R. and Grady, R. W., supra).

Desferrioxamine (DFO) is known to be useful in the treatment of other illness; its ability to chelate aluminum has been exploited in the treatment of Alzheimer's disease (Mclachlan, U.S. Pat. No. 4,419,365 issued Dec. 6, 1985). It has also been used to suppress *Plasmodium falciparum* malaria (Pollack, S. et al., *Proc. Soc. Exp. Diol. Med.* 184: 162–164, 1987).

OBJECTS OF THE INVENTION

It is an object of the present invention to provide a method for treating *Pneumocystis carinii* pneumonia (PCP) in mammals.

Another object of the present invention is to provide a method for treating PCP by administering to a mammal in need of such treatment therapeutically effective amounts of a pharmaceutically acceptable iron chelator.

Yet another object of the present invention is to provide a method for preventing the onset of PCP in a mammal in need of such prophylaxis by administering prophylactically a therapeutically effective amount of a pharmaceutically acceptable iron chelator.

A still further object of this invention is to provide a composition low in toxicity for treating or preventing the onset of PCP in mammals.

These and other objects of the present invention will be apparent to those of ordinary skill in the art in light of the present description and appended claims.

SUMMARY OF INVENTION

The present invention involves the discovery that iron chelators present an effective methodology for treating or preventing *Pneumocystis carinii* pneumonia (PCP) in mammals. The present inventors have found that iron chelators or chelating agents, such as hydroxamic acids, e.g., desferrioxamine, suppressed PCP in a rat model of the disease without the adverse side effects prevalent in the two current therapies. Additionally, such chelators have a prophylactic effect to which end they are preferably administered in a slow or in a sustained release medium.

The present invention provides a method of treating

*Pneumocystic carinii* pneumonia (PCP) which comprises administering to a mammal in need of such treatment an effective amount of a pharmaceutically acceptable iron chelator.

This invention also provides a method for preventing the onset of *Pneumocystis carinii* pneumonia (PCP) which comprises administering to a mammal in need of such prevention an effective amount of a pharmaceutically acceptable iron chelator.

This invention further provides a method of treating or preventing the onset of *Pneumocystis carinii* pneumonia which comprises administering to a mammal in need of such treatment a composition comprising the following components: (a) a pharmaceutically acceptable iron chelator; (b) a compound selected from trimethoprim/sulfamethoxazole, and pentamidine or compounds with related modes of action; and (c) a pharmaceutically compatible carrier or diluent, wherein the amounts of said component (a) and said component (b) in combination are effective in treating or preventing said pneumonia.

In one aspect, the present invention is directed to a composition for the treatment or prevention of *Pneumocystis carinii* pneumonia in mammals comprising the following components: (a) a pharmaceutically acceptable iron chelator; (b) a compound selected from trimethoprim/sulfamethoxazole and pentamidine; and (c) a pharmaceutically compatible carrier or diluent, wherein the amounts of said component (a) and said component (b) in combination are effective in treating or preventing said pneumonia.

In another aspect, this invention provides a composition for the treatment or prevention of *Pneumocystis carinii* pneumonia in mammals comprising:

(a) an amount of a pharmaceutically acceptable hydroxamic acid;

(b) an amount of pentamidine; and, (c) a pharmaceutically compatible carrier; wherein the total amounts of said components (a) and (b) in combination being effective in treating or preventing said pneumonia.

DETAILED DESCRIPTION OF THE INVENTION

All literature references and patents cited in this specification are hereby incorporated by reference in their entirety.

The present inventors have discovered that iron chelators can be used effectively alone, or in combination with other active agents, to treat *Pneumocystis carinii* pneumonia (PCP) in mammals. Previously, iron chelators, specifically desferrioxamine (DFO), had been used safely, i.e., with minimal adverse side effects, in patients, for example with beta thalassemia, who receive multiple blood transfusions and often suffer from iron overload as the result of such repeated transfusions.

As used herein, treatment is defined as suppression of PCP disease symptoms in mammals, e.g., individuals, with clinically apparent disease due to *P. carinii* and/or prevention of the disease in high-risk individuals. The latter class includes patients immunosuppressed due to AIDS as well as immunocompromised patients, i.e., those who are immunodeficient or immunosuppressed, e.g., genetically, or through disease or drug treatment. Mammals who are at risk to contract PCP also include mammals having at least partial acquired immunodeficiency and mammals having at least partial congenital immunodeficiency. Immunosuppressed host thus includes patients who through a genetic condition, disease or drug therapy have impaired, suppressed or inadequately developed immune systems. Specific nonlimiting examples of such patients are those suffering from AIDS or AIDS-Related complex (ARC-a prodrome of the disease), cancer patients undergoing X-ray or chemotherapy treatments and patients with a compromised immune system such as those individuals receiving immunosuppressive therapy because they have received or are preparing to receive an organ transplant, patients receiving immunosuppressive therapy for treatment of autoimmune disease, and individuals with congenital immunodeficiency, e.g., congenital agammaglobulinemia, Bruton's agammaglobulinemia, and Nezelof's syndrome.

The iron chelators of the present invention can be utilized for the treatment of mammals afflicted with PCP. Due to their high efficacy and lack of serious side effects, the iron chelators of the invention will also be particularly useful prophylactically for those at high risk of developing PCP as discussed above.

The iron chelators of the present invention are preferably administered in water soluble form such as in pharmaceutically acceptable salts or esters. For example, salts are contemplated in which the chelator activity resides in the cation or anion and the corresponding ion is pharmacologically suitable. Other forms of iron chelators include those in which the iron-binding moieties are blocked or modified so as to form a prodrug which on administration to (and/or upon being partially or totally metabolized by) the host will have iron-chelating activity.

The experiments reported in Examples 1 and 2 below were performed in a rat model of PCP. The course of the disease is very similar in chemically immunosuppressed rats and in humans with AIDS. All of the existing anti-*P. carinii* therapies were discovered with the aid of the rat model and this model is generally considered to be a good predictor of the response in humans.

Broadly, it is known in the art that PCP can be induced by immunosuppression alone although exposure to other animals with fulminant infection hastens infection in newly immunosuppressed animals. Generally, it takes from 6 months to 1 year to develop an intense, consistent level of infection within a colony of rats in which a portion of the rats are always maintained on an immunosuppressive regimen.

The animals used for the experiments described below were maintained in a room in which a series of other animals had been maintained on an immunosuppression regimen for more than a year and had developed heavy *P. carinii* infections. In addition, one week after initiation of immunosuppression, the rats were injected intratracheally with 0.05 ml of a tissue homogenate made from a rat lung heavily infected with *P. carinii*. In these experiments, immunosuppression was induced in the rats by biweekly injection of cortisone acetate. Following the development of an infection, the rats were subject to various treatment regimens, including maintenance on a low protein diet for the first 14 days of immunosuppression and antibiotic administration to protect against other infectious agents (see Example 1). In Example 2, the immunosuppression protocol was the same as in Example 1 except that the low protein diet was maintained for the entire experimental period and no amphotericin B was administered. Thereafter, the rats were sacrificed and examined for the existence of established *P. carinii* infection in the lungs. The number of cysts formed the basis for evaluating the efficacy of the treatment. Desferrioxamine (DFO) inhibited *P. carinii* cyst formation 85% in one experiment and over 93% in a second experiment.

In Example 1 below, a large DFO dosage was used, approximately 1 g/kg/day. It should be noted, however, that the effective dosage in a small mammal, e.g., a rodent, is expected to be significantly higher than that for large mammals, e.g., humans, on a mg/kg basis. Additionally, the administration of DFO to the test animals was by way of a single daily injection. The preferred administration to humans is a slow intravenous or subcutaneous infusion and such administration would result in a greater effect at a lower dosage. The amount or dosage of iron chelator to be administered to a mammal in accordance with the present invention may be determined by methods known to those skilled in the art (see, e.g., Jones, R., and Grady, R. W., supra).

The present invention provides a method of treating or preventing the onset of *Pneumocystis carinii* pneumonia (PCP), which comprises administering to a mammal in need of such treatment or prevention an effective amount of a pharmaceutically acceptable compound or composition displaying ironchelating activity in the bloodstream of the host. Non-limiting examples of suitable iron chelators include aromatic/aliphatic hydroxamic acids such as salicylhydroxamic acid (Aldrich Chemical Co., Milwaukee, Wis.); the mesylate salt of desferrioxamine (N-[5-[3-[(5-aminopentyl-)hydroxycarbamoyl]propionamido]pentyl]-3-[5-(N-hydroxyacetamido)pentyl]carbamoyl]propionohydroxamic acid monomethane sulfonate (DFO, desferrioxamine, Desferral®), available from CIBA Pharmaceutical Corp., Summit, N.J.; and N'N'-bis(2 3-dihydroxybenzoyl)-1,6-diaminohexane, described in Bhargava, K. K. et al., *J. Pharm. Sci.* 69: 986–989, 1980; catechols such as 2,3-dihydroxybenzoylglycine described in Ito, T. and Neilands, J. B., *J. Amer. Chem. Soc.* 80: 4645–4647, 1971; pyridones such as 1,2-dimethyl-3-hydroxypyrid -4-one described in Kontoghiorghes, G. J. and Sheppard, L., *Inorgan. Chim. Acta* 136: L11–12, 1987 and 1-methyl-3-hydroxy-pyrid-2-one described in Mohrle, H. and Weber, H., *Tetrahedron* 56: 3779–3785, 1970; thiosemicarbazones such as the thiosemicarbazones of picolinaldehyde described in Akiga, S., *Japan J. Exp. Med.* 26: 91–112, 1956; and 2,5-dihydroxybenzaldehyde, described in Ltaniyama, H. et al., *J. Pharm. Soc. Japan* 76:–1300–1303, 1956; and hydrazones such as pyridoxal isonicotinoyl hydrazone available from Porphyrin Products, Logan, UT and the guanyl hydrazone of 2-acetylpyridine described in Ulrich, P. C. et al., *Drug Dev. Res.* 2: 219–228, 1982. In addition, combinations of any of the foregoing iron chelators (having the property to chelate iron) may be administered in accordance with the present invention. In general. the iron chelators of the present invention bind at least one molecule of iron per molecule of iron chelator, e.g., DFO, although the iron-abstracting ability will vary with the given chelator. For example, thiosemicarbazones and bis(2,3-dihydroxybenzoyl) glycine (a catechol) bind two molecules of iron/molecule of chelator. Other iron chelators, such as salicylhydroxamic acid, 1,2-dimethyl-3-hydroxypyrid-4-one, and 1-methyl-3-hydroxypyrid-2-one bind three molecules of iron/molecule of chelator while N'N'-bis(2,3-dihydroxybenzoyl)-1,6-diaminohexane binds three molecules of iron/two molecules of chelator.

The route of administration depends on the particular chelator. In the case of desferrioxamine (DFO), parenteral administration is the preferred route. For example, DFO may be administered to the mammal or patient by subcutaneous injection. Subcutaneous injection may be carried out by means of a small portable pump capable of providing continuous infusion. In most other instances the iron chelator may be orally administered. Thus, for example, the following iron chelators are in general, orally administered: hydroxamic acids, e.g., acetohydroxamic acid (used in treatment of gallstones), Bufexamac® (4-butoxy-N-hydroxybenzeneacetamide; 2-(p-butoxyphenyl)acetohydroxamic acid), catechols, e.g., 2,3-dihydroxybenzoylglycine, pyridones, e.g., 1,2-dimethyl-3-hydroxypyrid-4-one, and 1-methyl-3-hydroxy-pyrid-2-one, thiosemicarbazones, e.g., thiosemicarbazones of picolinaldehyde and 2,5-dihydroxybenzaldehyde and hydrazones, e.g., pyridoxal isonicotinoyl hydrazone.

Those skilled in the art will readily appreciate that drug delivery systems may be employed in order to adapt a compound, i.e., iron chelator, for a particular route of administration. For example, desferrioxamine (DFO) is generally administered parenterally, e.g., subcutaneously and to a lesser extent, intravenously. Accordingly, DFO administration may be combined with pentamidine administration (generally intramuscularly) so that both compounds may be administered parenterally, e.g., intravenously, to treat or prevent the onset of PCP in a mammal. In addition, by "packaging" DFO in a pro-drug form, for example, by chemically modifying its structure by esterification, DFO may be administered orally, then acted upon by the gut and converted to an "active" form after absorption from the gut. Thus, if properly packaged (chemically modified), DFO could be administered orally in combination with other "oral" iron chelators.

The iron chelators of the present invention may be administered to mammals suffering from PCP in dosages broadly ranging between about 1 and about 260 mg/kg body weight per day and preferably between about 5 and 100 mg/kg body weight per day. For example, the dosage of desferrioxamine mesylate, could preferably range from about 0.2 to about 6 g daily, most preferably from about 0.5 to about 2.0 g daily. The iron chelators of the present invention may be administered orally up to 12 times daily (where applicable) or as intermittent/continuous, subcutaneous/intravenous infusions lasting 10 min to 24 hours as determined by the condition of the patient and stage of disease. A typical treatment regimen would comprise administration of 25 mg/kg body weight, 4 times per day. The duration and number of doses or treatments required to control a patient's disease will vary from individual to individual doses of DFO, up to 16 g per day can be tolerated by patients for a short course of intensive therapy.

In administering the iron chelator to the mammal or patients in order to treat or prevent the onset of PCP, pharmaceutically compatible carriers, diluents or excipients are employed. Such pharmaceutically compatible carriers include by way of example and not limitation, water, including sterile and deionized water, physiological saline, sodium bicarbonate and glucose. In the case of desferrioxamine (DFO), sterile water is the preferred pharmaceutically compatible carrier.

In other embodiments of this invention, iron chelators, such as desferrioxamine (DFO), may be employed in combination with other compounds previously used in the treatment or prevention of *Pneumocystis carinii* pneumonia. Such previously used compounds include but are not limited to: inhibitors of dihydrofolate reductase such as trimethoprim, methotrexate, trimetrexate, piritrexim and others either singly or in combination with compounds that interfere with the metabolism of para-aminobenzoic acid such as sulfamethoxazole, dapsone and other sulfonamides and sulfones, i.e., "sulfa drugs"; polyamine biosynthesis inhibitors such as DL-alpha-difluoromethylornithine, other ornithine analogues and bis-benzyl polyamines; clindamycin and primaquine, singly or together; pentamidine and other diamidines such as diminazene (berenil) and 1,4-di(4'-amidinophenoxy)butane; and corticosteroids or other anti-inflammatory or immunosuppressive agents. Such previously used compounds include dihydrofolate reductase (DHFR) inhibiting compounds, i.e., compounds that inhibit the activity or formation of DHFR, such as trimethoprim/sulfamethoxazole (TMP/SMZ) and pentamidine. In combining iron chelators in compositions with other compounds, the severe toxic effects of such other compounds may be reduced as a consequence of employing lesser amounts of such compounds. Accordingly, amounts less than the recognized effective amounts of 20 mg/kg/day and 100 mg/kg/day, in the case of TMP and SMZ, respectively, or 4 mg/kg/day in the case of pentamidine may be employed according to this invention. For use in combination with an appropriate iron chelator, TMP/SMZ may be used over a range of 1 to 20 mg TMP/kg/day and 5 to 100 mg SMZ/kg/day for 5 days to 3 weeks, and pentamidine (as the isethionate, methanesulfonate or other salt) over a range of 0.1 to 2.0 mg/kg/day for 1 to 14 days to treat or prevent PCP in mammals.

It should be understood that the amounts of component (a) and component (b) in combination which are effective in treating or preventing PCP, also embraces the situation where either component alone, might or might not, be effective in treating or preventing the pneumonia. It is expected that the effect or benefit of using a combination of iron chelator with either TMP/SMZ or pentamidine will at least be additive in that the mechanisms of action are believed to be different. Accordingly, the effect of the iron chelator should not interfere with the effect of component (b), i.e., TMP/SMZ or pentamidine, and vice versa.

In another feature of this invention, the iron chelator and/or TMP/SMZ (and/or pentamidine) may be administered in combination with the administration of a diet deficient in iron to treat or prevent the onset of PCP in mammals. The amount of iron in the diet required to produce such a deficiency in a mammal will, of course, vary according to the subject but such amounts are ascertainable by those skilled in the art.

This invention further provides a method of treating or preventing the onset of *Pneumocystis carinii* pneumonia which comprises administering to a mammal in need of such treatment or prevention a composition comprising the following components: (a) a pharmaceutically acceptable iron chelator; (b) a compound selected from trimethoprim/sulfamethoxazole, pentamidine or other agent or combination of agents known to be active against PCP; and (c) a pharmaceutically compatible carrier or diluent, wherein the amounts of said component (a) and said component (b) in combination are effective in treating or preventing said pneumonia. Examples of iron chelators, and amounts or dosages, including such preferred amounts and dosages of iron chelators, TMP/SMZ, pentamidine, modes of administration and pharmaceutically compatible carriers or diluents have been described above. It should be understood that the amount of either component (a) or component (b) alone, might or might not be effective in treating or preventing said pneumonia. The combination of the two components, (a) and (b), however, is effective for such treatment or prevention.

The present invention concerns a composition for the treatment or prevention of *Pneumocystis carinii* pneumonia in mammals comprising: (a) an amount of a pharmaceutically acceptable iron chelator; (b) an amount of a compound selected from trimethoprim/sulfamethoxazole (TMP/SMZ) and pentamidine, and a pharmaceutically compatible carrier, such as water, including, sterile or deionized Water, physiological saline, sodium bicarbonate, and glucose.

This invention further concerns a composition for the treatment or prevention of *Pneumocystis carinii* pneumonia in mammals comprising:

(a) an amount of a pharmaceutically acceptable hydroxamic acid;

(b) an amount of pentamidine; and (c) a pharmaceutically compatible carrier; wherein the total amounts of said components (a) and (b) in combination are effective in treating or preventing said pneumonia.

The iron chelators (a) in this composition include without limitation hydroxamic acids, preferably, N-[5-[3-[(5-aminopentyl)hydroxycarbamoyl]propionamido]pentyl]-3-[[5-(N-hydroxyacetamido)pentyl]carbamoyl]propionohydroxamic acid monomethane sulfonate (DFO), catechols, catecholates, pyridones, thiosemicarbazones and hydrazones and combinations of any of the foregoing that have the property to chelate iron. Effective amounts of the iron chelator may range from about 1 to about 260 mg/kg body weight per day, preferably from about 5 to about 100 mg/kg body weight, per day. When DFO is employed, the effective amount may range from about 0.2 to about 6 g daily, preferably from about 0.5 to about 2.0 g daily.

The amount of the compound (b) in the composition, e.g., a dihydrofolate reductase inhibiting compound, e.g., TMP/SMZ or pentamidine, may vary from about 1 to about 100 mg/kg per day, i.e., from about 1 to about 20 mg TMP/kg/day; from about 3 to about 100 mg SMZ/kg/day; and from about 0.1 to about 2.0 mg pentamidine/kg/day. Those skilled in the art will appreciate that the amount of TMP/SMZ or pentamidine, as the case may be, may be less than the effective amount of these reducing the toxic side-effects associated with their administration.

The components, i.e., iron chelator and compound selected from TMP/SMZ and pentamidine, may be administered in accordance with the present invention in formulations such as liquids, e.g., suspensions, dispersions, which include sterile aqueous solutions or dispersions, or sterile powders for the extemporaneous preparation of sterile injectable solutions or dispersions. The formulations may also be administered as tablets, which are also available commercially, e.g., sulfamethoxazole with trimethoprim tablets 400 mg w/80 mg, are available from Barr Laboratories, Inc., Northvale, N.J. 07647.

In the case of desferrioxamine (DFO), particularly the mesylate salt, the compound may be prepared for parenteral, i.e., intramuscular, intravenous or subcutaneous administration by dissolving in sterile water and making sure that the drug is completely dissolved before administering.

The use of iron chelators in the treatment of PCP may also yield additional unexpected advantages. It has been shown for example, that DFO decreases collagen accumulation and lessens the severity of lung fibrosis induced by the antineoplastic agent bleomycin (Chandler, D.B. and Fulmer, J. D., *Am. Rev. Respir. Dis.*, 131: 596–598, 1984).

The present invention is further described below in specific working examples which are intended to illustrate the invention without limiting the scope thereof.

EXAMPLE 1

Treatment of PCP with DFO in a Rat Model for the Disease

Two examples of the efficacy of iron chelators in the treatment of PCP in a rat model are presented. These examples use DFO as a model compound. For the two examples, slightly different protocols were used for inducing immunosuppression in the rats and thus producing PCP.

The effects of DFO on rats suffering from PCP was examined as follows. To initiate immunosuppression, and continuing for the entire experimental period, rats (5 per group) were given twice Weekly subcutaneous injections of cortisone acetate (25 mg/per injection Cortone®, Merck Sharpe and Dohme, West Point, Pa.). To ensure complete immunosuppression, the rats were maintained on a low protein diet (8.5% protein, W. F. Fisher and Sons, Bound Brook, N.J.) for the first 14 days of the experiment. All food, bedding, cages and water bottles were sterilized before use. From the initiation of immunosuppression and for the entire experimental period, protection from other infectious agents was provided by the inclusion of 3.56 g (oxytetracycline HCl, Polyotic® Pfizer, Agricultural Division, New York, N.Y.) per liter of drinking water and by subcutaneous injection of 2.5 mg amphotericin B (Fungizone®, E. R. Squibb and Sons, Inc. Princeton, N.J.).) per animal twice weekly. The initial weight of the rats was about 180 g but this declined by about 35% during the course of the experiments.

Desferrioxamine mesylate (DFO, desferrioxamine, Desferral®, CIBA Pharmaceutical Co., Summit, N.J.) was administered at the indicated dose by subcutaneous injection after reconstitution with 2.0 ml sterile water per vial, i.e., according to the manufacturer's instructions. The entire daily dose was given in a single injection.

The intensity of the *P. carinii* infection was judged from smears made from homogenates of rat lung. This procedure involved the removal of both lungs from a rat and then pressing the lungs through a stainless steel garlic press. The extruded lung tissue was then suspended in 5.0 ml of a buffer comprising 0.1M $Na_2HPO_4$ (Sigma Chemical Co., St. Louis, Mo.), 0.073M NaCl (Sigma Chemical Co., St. Louis, Mo.), 100 mM ethylenediaminetetraacetate (Mallinckrodt Inc., St. Louis, Mo.), pH 7.4. The suspended lung tissue was then forced through a stainless steel tea strainer with the aid of the plunger from a 5-ml disposable syringe (Becton Dickinson and Co., Rutherford, N.J.). A smear of the homogenate was prepared and stained with cresyl echt violet (Roboz Surgical Instrument Corp., Washington, D.C.) to reveal *Pneumocystis carinii* cysts (as described in Bowling et al., *Am. J. Med. Technol.*, 39:267–268, 1973). Special attention was paid to maintain the pH of the stain at 1.5. The process of staining for *P. carinii* cysts involved first air drying then heat fixing the smear. They were then held 10 minutes in a coplin jar (Fisher Scientific, Springfield, N.J.) containing 60 ml glacial acetic acid (Fisher Scientific) and 20 ml concentrated sulfuric acid (Fisher Scientific) and frequently agitated. The slides were rinsed in tap water for 8 minutes and placed for 25 minutes in another coplin jar containing the staining solution made of 0.1 g cresyl echt violet, 60 ml 0.1N HCl and 40 ml 0.1M $NaH_2SO_4$. The staining solution had been made at least 24 hours before use, filtered through fluted filter paper (Whatman 2 V, Fisher Scientific) and the pH adjusted to 1.5. The slide was then rinsed in tap water and placed for 2 minutes in a coplin jar containing 0.01 g naphthol yellow (Aldrich Chemical Co., Milwaukee, Wis.) and 100 ml of 1% glacial acetic acid. The slides were rinsed, air-dried and examined for cysts with a 100× oil immersion lens. The cysts in 250 fields were counted and this count was the PCP intensity score.

Experimental therapies were begun 62 days after initiation of immunosuppression. The experimental therapies were given for 3 weeks and the animals were then sacrificed and examined for *P. carinii* in the lungs.

TABLE 1

EVALUATION OF DESFERRIOXAMINE
IN A RAT MODEL OF *Pneumocystis carinii* PNEUMONIA

| Treatment | Mean Daily Drug Dosage (mg/kg-1 day) | Individual Animal Infections After 3 Weeks (cysts/250 fields) | Mean Infection ± SEM (cysts/250 fields) |
|---|---|---|---|
| None (Negative Control) | N/A* | 37<br>74<br>287<br>27<br>58 | 96.6 ± 48.3 |
| Trimethoprim + Sulfamethoxazole in Drinking Water (Positive Control) | 26.2 + 130.9 | 0<br>0<br>0<br>0<br>0 | 0 ± 0 |
| Desferrioxamine s.c. | 1000 | 13<br>34<br>17<br>7<br>4 | 15.0 ± 5.3 |

* = Not Applicable

As can be seen from the data in Table I, while the TMP/SMZ treatment was highly effective, DFO suppressed PCP by an average of 85% in the rat model. Therefore, DFO provided a substantial reduction in the *P. carinii* population without the side effects attendant with TMP/SMZ treatment and thus permits a viable alternative (or adjunct) to TMP/SMZ therapy.

EXAMPLE 2

The data for Example 2 are presented in Table 2. The immunosuppression protocol for Example 2 was the same as in Example 1 except the low protein diet was maintained for the entire experimental period, no amphotericin B was administered, and infection was initiated solely by exposure via the room air to other animals which had been placed on immunosuppression earlier.

The effect of a range of DFO dosages is presented in Table 2.

TABLE 2

FURTHER EVALUATION OF DESFERRIOXAMINE
IN A RAT MODEL OF *Pneumocystis carinii* PNEUMONIA

| Treatment | Drug Dosage (mg kg-1) | Daily Animal Cyst Count (cysts/250 fields) | Individual Mean Cyst Count +SEM (cysts/250 fields) |
|---|---|---|---|
| None (Negative Control) | | 0<br>6250<br>123 | 1451 ± 762 |

TABLE 2-continued

FURTHER EVALUATION OF DESFERRIOXAMINE
IN A RAT MODEL OF *Pneumocystis carinii* PNEUMONIA

| Treatment | Drug Dosage (mg kg-1) | Daily Animal Cyst Count (cysts/250 fields) | Individual Mean Cyst Count +SEM (cysts/250 fields) |
|---|---|---|---|
|  |  | 37 |  |
|  |  | 4500 |  |
|  |  | 609 |  |
|  |  | 104 |  |
|  |  | 850 |  |
|  |  | 589 |  |
| desferrioxamine | 1000 | 13 | 9 ± 3 |
|  |  | 15 |  |
|  |  | 20 |  |
|  |  | 0 |  |
|  |  | 10 |  |
|  |  | 4 |  |
|  |  | 5 |  |
|  |  | 2 |  |
| desferrioxamine | 500 | 16 | 27 ± 10 |
|  |  | 77 |  |
|  |  | 7 |  |
|  |  | 0 |  |
|  |  | 27 |  |
|  |  | 20 |  |
|  |  | 60 |  |
|  |  | 8 |  |
| desferrioxamine | 250 | 179 | 106 ± 46 |
|  |  | 95 |  |
|  |  | 71 |  |
|  |  | 4 |  |
|  |  | 4 |  |
|  |  | 48 |  |
|  |  | 343 |  |

From the data shown in Table 2 above, it can be seen that DFO significantly inhibited cyst formation in the lungs of treated animals at all dosages (250–1000 mg kg$^{-1}$).

EXAMPLE 3

In this experiment, a pyridone iron chelator, 1,2-dimethyl-3-hydroxypyrid-4-one (DMHP) (Kontoghiorghes, G. J. and Sheppard, L., Supra) is administered to an immunosuppressed rat model. The rat subjects are immunosuppressed by following the immunosuppression protocol of Example 2. DMHP is administered orally or intrapentoneally to rate subjects in the following amounts (dosages): 10, 20, 40, 75, 150, 300 and 600 mg/kg/day. DHMP is prepared as the hydrochloride salt by dissolving in water with the total volume administered to the rat subjects being 1 ml/100 g body weight. The evaluation of the efficacy of DMHP is carried out according to the evaluation set forth in Example 2.

What is claimed is:

1. A method of treating pneumonia caused by *Pneumocystis carinii* comprising administering (a) a pharmaceutically acceptable iron chelator and (b) pentamidine wherein the amounts of (a) and (b) in combination are effective in treating pneumonia caused by *Pneumocystis carinii*.

2. A method of treating pneumonia caused by *Pneumocystis carinii* comprising administering (a) pentamidine and (b) a hydroxamic acid wherein the amounts of (a) and (b) in combination are effective in treating pneumonia caused by *Pneumocystis carinii*.

3. A method of preventing the onset of pneumonia caused by *Pneumocystis carinii* comprising administering (a) a pharmaceutically acceptable iron chelator and (b) pentamidine wherein the amounts of (a) and (b) in combination are effective in preventing pneumonia caused by *Pneumocystis carinii*.

4. A method of preventing the onset of pneumonia caused by *Pneumocystis carinii* comprising administering (a) pentamidine and (b) a hydroxamic acid wherein the amounts of (a) and (b) in combination are effective in preventing pneumonia caused by *Pneumocystis carinii*.

5. A composition for the treatment or prevention of pneumonia caused by *Pneumocystis carinii* in mammals comprising:

(a) an amount of a pharmaceutically acceptable hydroxamic acid;

(b) an amount of pentamidine; and (c) a pharmaceutically compatible carrier, wherein the total amounts of said components (a) and (b) in combination are effective in treating or preventing said pneumonia.

* * * * *